US012582369B2

(12) United States Patent
Asai et al.

(10) Patent No.: US 12,582,369 B2
(45) Date of Patent: Mar. 24, 2026

(54) MAMMOGRAPHY APPARATUS

(71) Applicants: KINKI UNIVERSITY, Higashiosaka (JP); Canon Medical Systems Corporation, Otawara (JP)

(72) Inventors: Yoshiyuki Asai, Osakasayama (JP); Mika Yamamuro, Osakasayama (JP); Haruki Iwai, Otawara (JP); Naoko Kuratomi, Sakura (JP); Yoshimasa Kobayashi, Nasushiobara (JP); Rie Ikezaki, Sakura (JP)

(73) Assignees: KINKI UNIVERSITY, Higashiosaka (JP); Canon Medical Systems Corporation, Otawara (JP)

( * ) Notice: Subject to any disclaimer, the term of this patent is extended or adjusted under 35 U.S.C. 154(b) by 188 days.

(21) Appl. No.: 18/526,092

(22) Filed: Dec. 1, 2023

(65) Prior Publication Data

US 2024/0180508 A1      Jun. 6, 2024

(30) Foreign Application Priority Data

Dec. 1, 2022      (JP) ................................. 2022-193023

(51) Int. Cl.
*A61B 6/04* (2006.01)
*A61B 6/50* (2024.01)

(52) U.S. Cl.
CPC ............ *A61B 6/502* (2013.01); *A61B 6/0414* (2013.01)

(58) Field of Classification Search
CPC ..... A61B 6/0414; A61B 6/502; A61B 6/5217; A61B 6/54; A61B 6/542; A61B 5/4312; A61B 6/50; A61B 8/0825; A61B 6/482; A61B 8/406; A61B 8/5223; A61B 5/004; A61B 5/0091; A61B 8/467; A61B 8/13; A61B 8/5215; G06T 2207/30068; G06T 2207/10116; G06T 2207/10081; G06T 7/0016; G06T 7/97
See application file for complete search history.

(56) References Cited

U.S. PATENT DOCUMENTS

2018/0279982 A1* 10/2018 Fukuda ................ A61B 5/1072

FOREIGN PATENT DOCUMENTS

JP      2011-115368 A      6/2011

* cited by examiner

*Primary Examiner* — Don K Wong
(74) *Attorney, Agent, or Firm* — Oblon, McClelland, Maier & Neustadt, L.L.P.

(57) ABSTRACT

According to one embodiment, a mammography apparatus includes processing circuitry. The processing circuitry is configured to acquire, as information on preliminary X-ray imaging for a breast of a subject, first information including at least one of an imaging condition, breast state information indicating a state of the breast, and/or information on the subject. The processing circuitry is configured to calculate an index for the breast based on the first information.

16 Claims, 5 Drawing Sheets

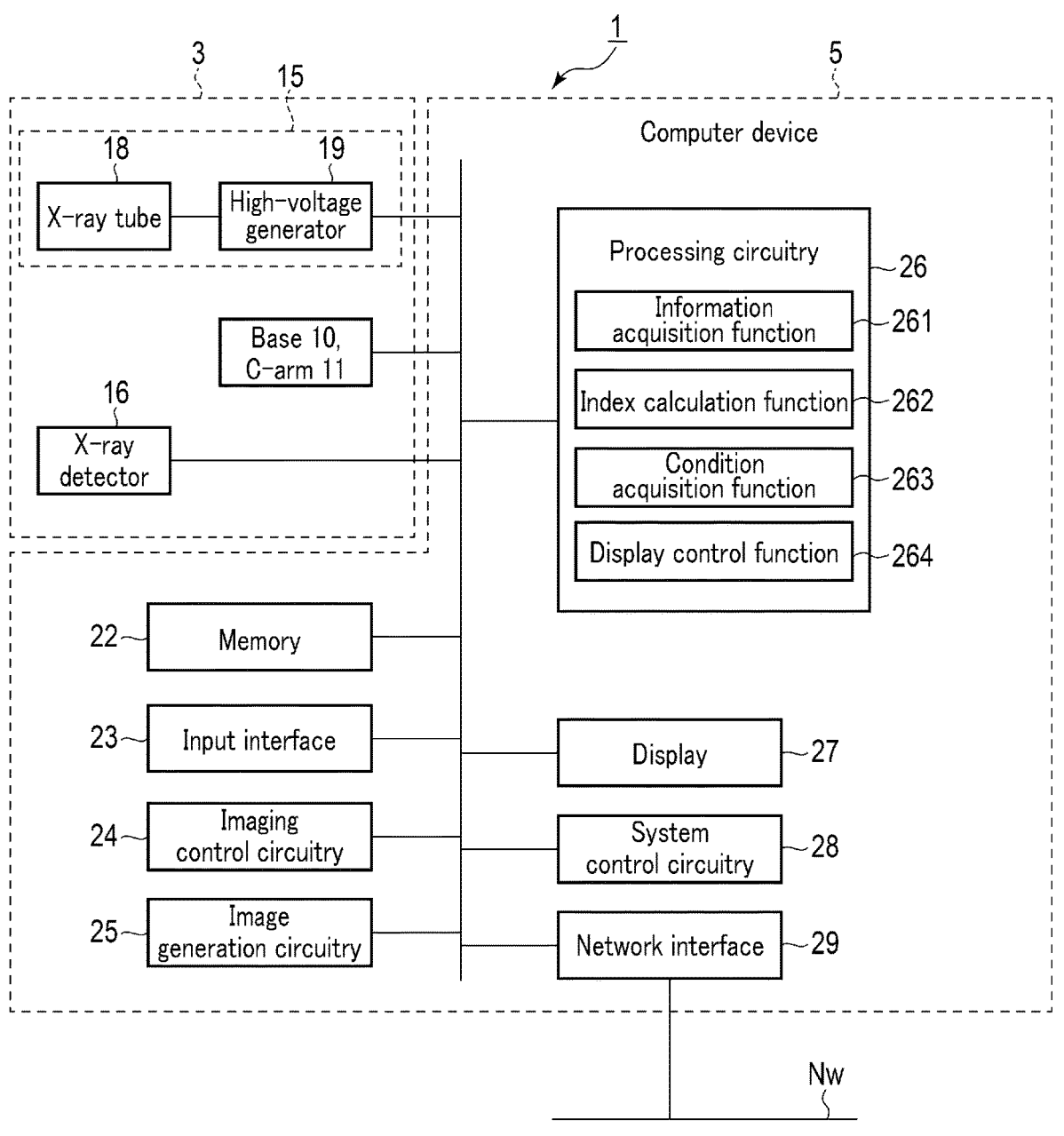
F I G. 1

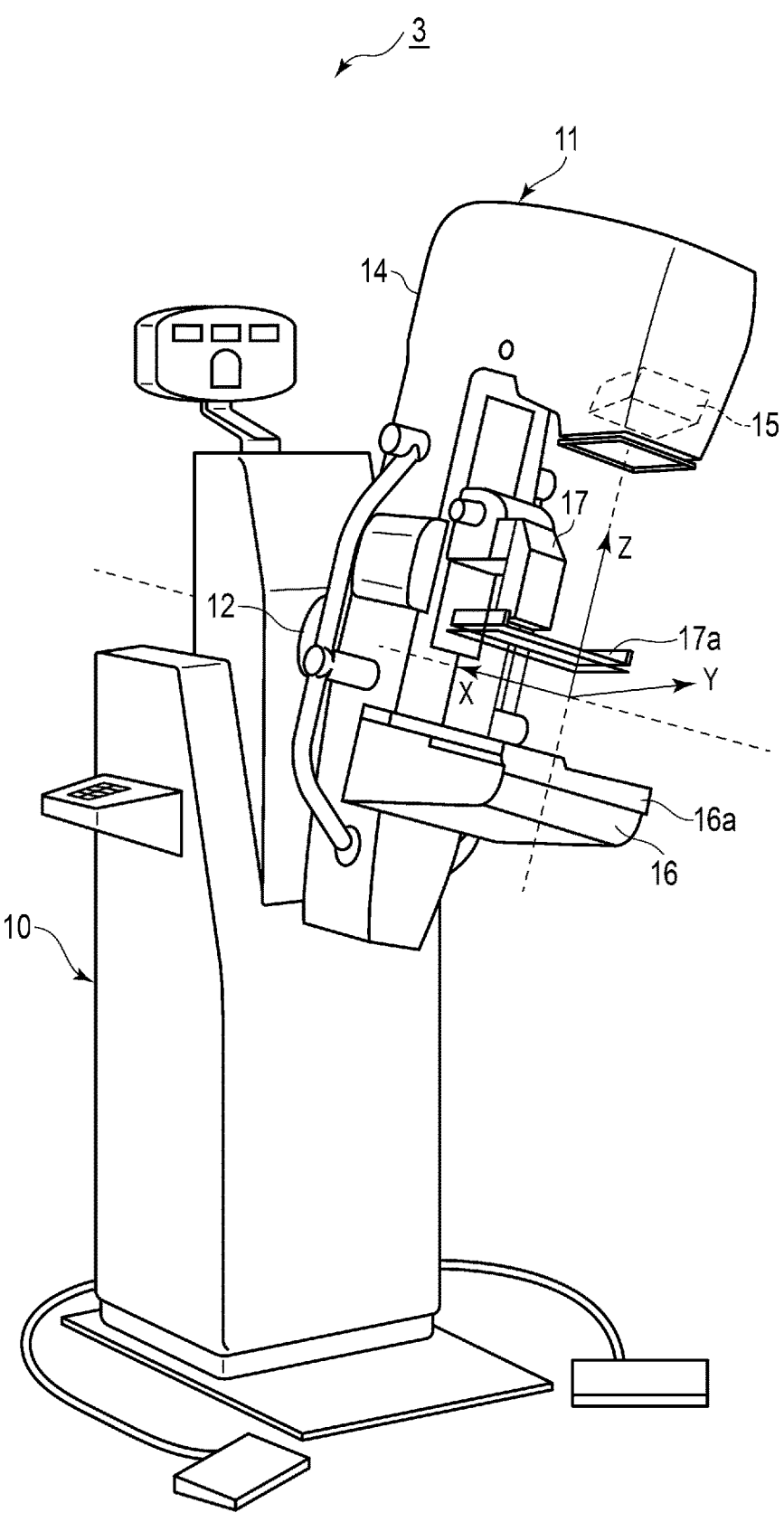
F I G. 2

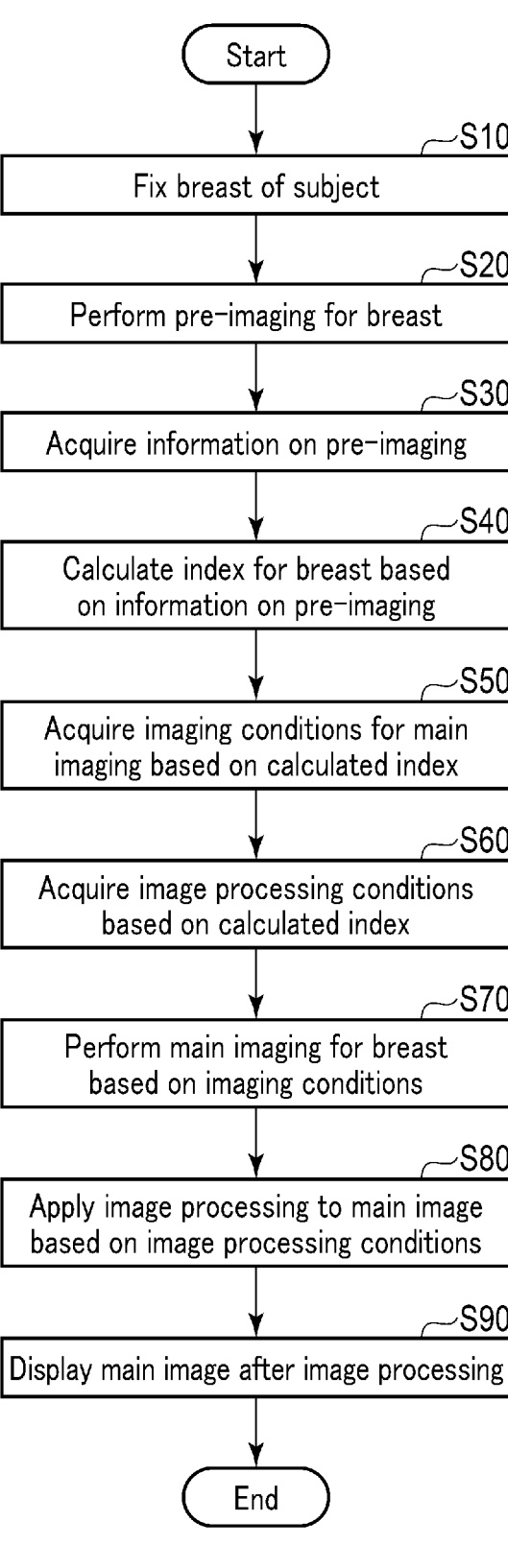
F I G. 3

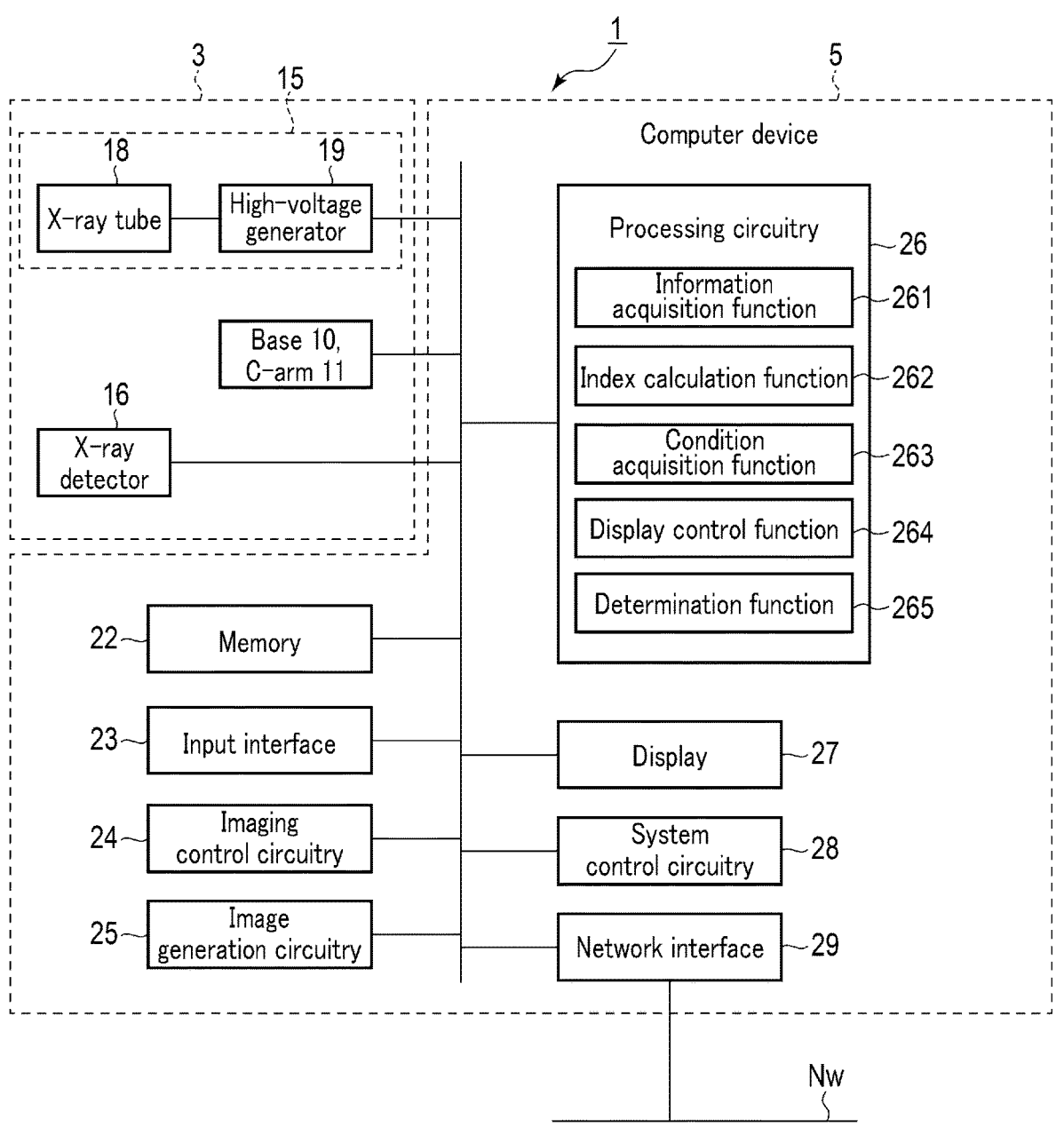
F I G. 4

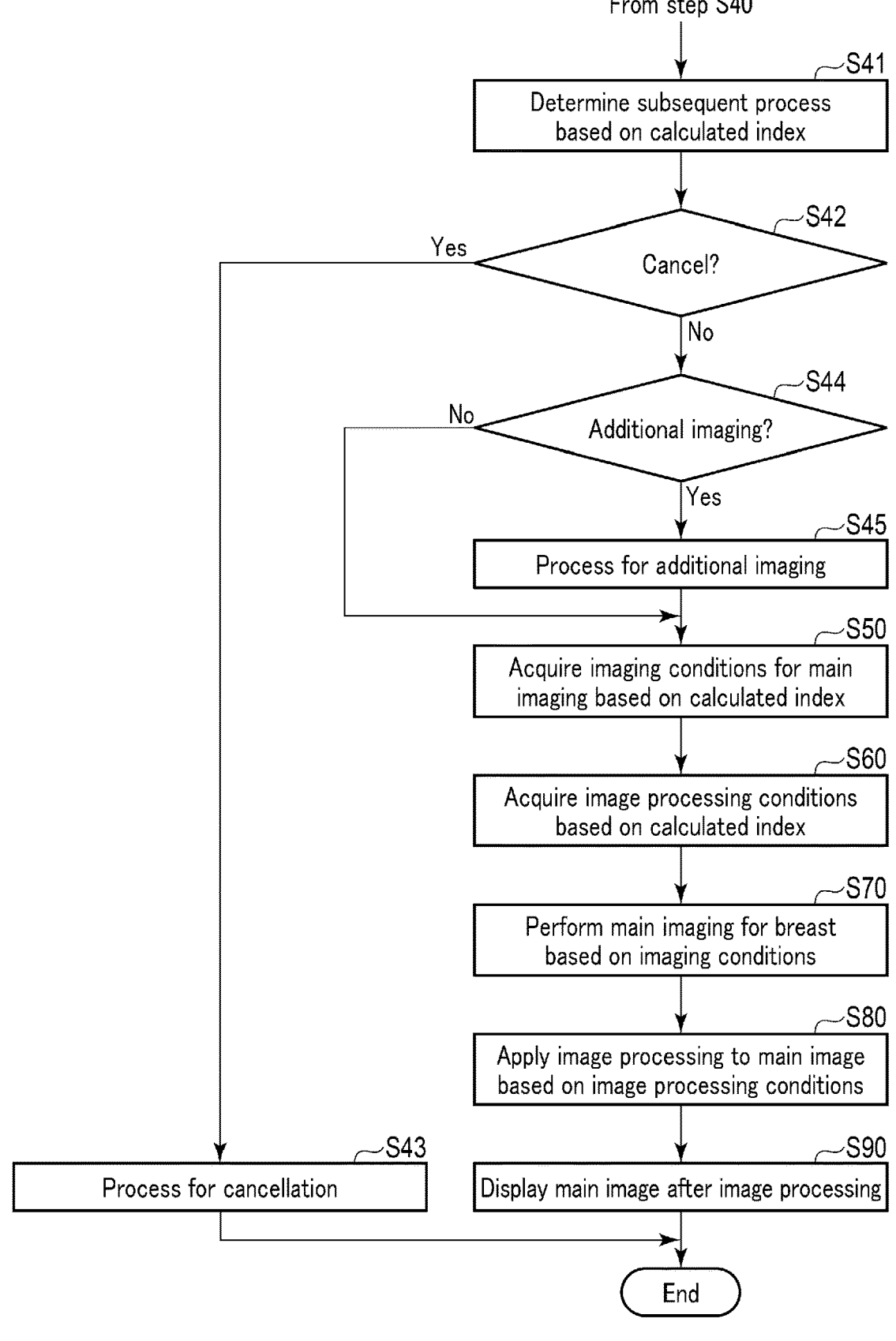
F I G. 5

MAMMOGRAPHY APPARATUS

CROSS-REFERENCE TO RELATED APPLICATION (S)

This application is based upon and claims the benefit of priority from the prior Japanese Patent Application No. 2022-193023, filed Dec. 1, 2022, the entire contents of which are incorporated herein by reference.

FIELD

Embodiments described herein relate generally to a mammography apparatus.

BACKGROUND

A mammography apparatus compresses the breast of a subject and holds it still to perform X-ray imaging twice, namely, a preliminary X-ray imaging (hereinafter, "pre-imaging") and a main X-ray imaging for the breast in this order. The mammography apparatus determines imaging conditions for the main imaging, image processing conditions, etc., through automatic exposure control (AEC) that uses only the information directly obtained from the pre-imaging with weak X-ray irradiation (hereinafter, "direct information"). The direct information here refers to the thickness of the breast under compression, the pixel value of an image acquired by the pre-imaging (hereinafter, a "pre-image"), and so on. The mammography apparatus conducts the main imaging according to the determined imaging conditions, and processes an image acquired by the main imaging (hereinafter, a "main image") according to the image processing conditions. The mammography apparatus thus provides an X-ray image which allows doctors to easily make their interpretation. Also, it is current practice that if the result of measuring the breast density from a main image indicates a dense breast, the subject is encouraged to take an additional ultrasound test or is informed of a risk of developing cancer in the future.

Such a mammography apparatus generally works well but the inventors of the present invention see room for improvement as the use of only the direct information obtained from pre-imaging does not always assure successful determination of appropriate conditions for operations following the pre-imaging. As one example, even in the case of handling breasts of the same thickness, appropriate imaging conditions and image processing conditions vary depending on breast compositions, etc. Supposing an instance where a fatty breast having a thickness of 5 cm is handled, it is preferable to be able to determine imaging conditions that stipulate a reduced radiation dose and image processing conditions that darken the fatty area, since the breast includes a relatively small amount of mammary gland tissues serving as high X-ray absorbers. On the other hand, in an instance where a dense breast having the same 5 cm thickness is handled, it is preferable to be able to determine imaging conditions that stipulate an increased radiation dose and image processing conditions that lighten the mammary gland region. It is therefore desired that a mammography apparatus be capable of acquiring not only the direct information obtained from pre-imaging but also information for determining more appropriate conditions.

BRIEF DESCRIPTION OF THE DRAWINGS

FIG. 1 is a block diagram showing an exemplary configuration of a mammography apparatus according to an embodiment.

FIG. 2 is a perspective view showing, as one example, an appearance of an X-ray imaging stand according to an embodiment.

FIG. 3 is a flowchart for explaining operations according to an embodiment.

FIG. 4 is a block diagram showing a configuration of a mammography apparatus according to a modification of an embodiment.

FIG. 5 is a flowchart for explaining operations according to a modification of an embodiment.

DETAILED DESCRIPTION

In general, according to one embodiment, a mammography apparatus includes processing circuitry. The processing circuitry is configured to acquire, as information on preliminary X-ray imaging for a breast of a subject, first information including at least one of an imaging condition, breast state information indicating a state of the breast, and/or information on the subject. The processing circuitry is configured to calculate an index for the breast based on the first information.

A mammography apparatus according to an embodiment will be described with reference to the drawings.

FIG. 1 is a block diagram showing a configuration of such a mammography apparatus according to an embodiment, and FIG. 2 is a perspective view showing one example of the appearance of an X-ray imaging stand in the mammography apparatus. This mammography apparatus 1 includes the X-ray imaging stand 3 and a computer device 5.

The X-ray imaging stand 3 includes a base 10 and a C-arm 11. The C-arm 11 is attached to a shaft 12 projecting from the base 10. The C-arm 11 is thus supported by the base 10 so that it can rotate about the center of the shaft 12, i.e., a central axis X for rotation. Rotation of the C-arm 11 enables operations for normal imaging and tomosynthesis imaging based on various projection directions including a cranio-caudal (CC) direction, a mediolateral (ML) direction, and a mediolateral oblique (MLO) direction. Tomosynthesis is an imaging technique which generates multiple tomograms by three-dimensionally reconstructing medical images acquired at multiple angles along with the movement of an X-ray tube 18. The tomosynthesis imaging of a breast can create tomograms involving reduced overlaps of mammary glands.

The C-arm 11 is constituted by an arm body 14 furnished with an X-ray generator 15, an X-ray detector 16, and a compression unit 17. The X-ray generator 15 and the X-ray detector 16 are arranged at the respective ends of the arm body 14. The compression unit 17 is arranged midway between the X-ray generator 15 and the X-ray detector 16.

The X-ray generator 15 includes the aforementioned X-ray tube 18 and a high-voltage generator 19. The X-ray tube 18 receives a tube voltage application and a filament current supply from the high-voltage generator 19 and output X-rays toward the compression unit 17 for a predetermined X-ray continuation period. The tube voltage for application and the X-ray continuation period are adjusted into values that are suitable for imaging operations, based on control signals received from later-described imaging control circuitry 24.

The X-ray tube 18 includes a cathode filament and an anode. The anode may be, for example, a Mo anode formed of molybdenum (Mo), a Rh anode formed of rhodium (Rh), a Mo—Rh anode formed of a mixture of Mo and Rh, and so on. Multiple such anodes may be provided so that they can discretionarily be switched according to control signals from the imaging control circuitry 24.

With the filament current supply, the cathode filament is heated and generates thermal electrons. With the tube voltage application between the cathode filament and the anode, the generated thermal electrons are caused to collide with the anode. The thermal electrons colliding with the anode thus generate X-rays. As the thermal electrons fly and collide with the anode, a tube current flows. The tube current is adjusted by the filament current. An X-ray radiation dose during an imaging operation is controlled by adjusting a tube current-time product, which is a product of a tube current multiplied by an X-ray continuation period (time), according to control signals from the imaging control circuitry 24.

The X-ray tube 18 is furnished with a radiation quality filter for altering the radiation quality of the X-rays generated. The radiation quality filter may include a Mo filter formed of Mo, a Rh filter formed of Rh, an Al filter formed of aluminum (Al), a filter formed of a mixture of such materials, and so on. A multiple of such filters may be provided so that they can discretionarily be switched according to control signals from the imaging control circuitry 24.

The compression unit 17 includes a compression plate 17a which is supported by the C-arm 11 so as to face a detection plane 16a of the X-ray detector 16 and be capable of making approaching and separating movement with respect to this detection plane 16a along an axis Z orthogonal to the rotational central axis X of the C-arm 11. The compression unit 17 moves the compression plate 17a according to control signals from the imaging control circuitry 24 so that the breast of a subject is pressed against the detection plane 16a and set to a predetermined thickness state.

The X-ray detector 16 is supported by the C-arm 11 so as to be capable of approaching and separating from the X-ray tube 18 along the imaging axis (i.e., the axis Z) connecting the plane center of the detection plane 16a and the focal point of the X-ray tube 18. The X-ray detector 16 may be a digital detector such as a flat panel detector which detects X-rays transmitted through the breast. Such a digital detector includes multiple direct-conversion type semiconductor detecting elements for converting incident X-rays directly into electrical signals, or multiple indirect-conversion type semiconductor detecting elements for converting incident X-rays into light by fluorescent components and then converting the light into electrical signals. These semiconductor detecting elements are arrayed in a two-dimensional grid pattern. In addition to such semiconductor detecting elements, e.g., photodiodes, the digital detector includes an amplifier circuit and an A/D converter circuit. Thus, signal charges occurring at the multiple semiconductor detecting elements upon X-ray incidence are relayed through the amplifier circuit and the A/D converter circuit, and output to the computer device 5 as output signals.

The computer device 5 includes, for use with the X-ray imaging stand 3, a memory 22, an input interface 23, the imaging control circuitry 24 mentioned above, image generation circuitry 25, processing circuitry 26, a display 27, system control circuitry 28, and a network interface 29.

The memory 22 includes a memory main part for storing electrical information, such as a read only memory (ROM), a random access memory (RAM), a hard disk drive (HDD), and/or an image memory, and peripheral circuitry associated with the memory main part, such as a memory controller and/or a memory interface. The memory 22 stores various pieces of information and data items including X-ray images (medical images) such as pre-images and main images, programs, and trained models. Examples of the main images include mammograms acquired under normal imaging, and multiple projection image data items and multiple tomograms acquired under tomosynthesis imaging. A program or programs stored in the memory 22 may cause a computer to implement, for example, an information acquisition function, an index calculation function, a condition acquisition function, a display control function, and a determination function. Note that the information acquisition function, the index calculation function, the condition acquisition function, the display control function, and the determination function here correspond to the respective functions of the processing circuitry 26 described later. Trained models stored in the memory 22 may include a trained model that has undergone, for example, an artificial-intelligence (AI)-utilized training process using datasets containing information on the pre-imaging of a breast and indexes for the breast. Note that the model training process is not limited to the utilization of AI, but the training process may instead or additionally adopt any of a statistical approach such as the conventional regression analysis and support vector machine techniques, and a machine learning approach such as machine learning and deep learning techniques. The datasets here each include information on the pre-imaging of a breast as input data and an index for the breast as output data, which may be prepared in advance. The trained model is adapted to output, based on information on the pre-imaging of a breast, an index for the breast. Such an index for a breast may represent a classification result for the breast or a continuous value for the breast.

The input interface 23 is realized by one or more components for an operator to input various instructions, commands, information sets, selections, settings, etc., to the computer device 5, and such components include a trackball, switch buttons, a mouse, a keyboard, a touch pad which allows input operations through contacting of the operation screen, and a touch panel display which integrates a display screen and a touch pad. The input interface 23 is connected to the imaging control circuitry 24, the processing circuitry 26, etc., so that it converts input operations received from the operator into electrical signals and outputs the electrical signals to the imaging control circuitry 24, the processing circuitry 26, etc. In the disclosure related to the computer device 5 herein, an "operation of the operator" or the like may be taken to mean an "operation on the input interface 23 by the operator". Note also that, in the disclosure herein, the input interface 23 is not limited to physical operation components such as a mouse, a keyboard, or the like. Examples of the input interface 23 also include electrical signal processing circuitry that receives an electrical signal corresponding to an input operation from an external input device separate from the mammography apparatus, and outputs this electrical signal to the imaging control circuitry 24, the processing circuitry 26, etc.

According to an operation of the operator, the input interface 23 outputs subject information provided from, for example, a radiology information system (RIS) (not shown in the figures) so that the subject information is stored in the memory 22. Such subject information contains, for example, a subject ID, an examination part, an examination purpose, an age, a body height, a body weight, a body mass index (BMI), etc. The input interface 23 may also serve as an operation panel for setting, for example, imaging conditions (a tube voltage, a tube current-time product, anode materials, radiation quality filter materials, a breast thickness, a distance between the X-ray focal point and the X-ray detector, a magnification ratio, etc.) and image processing conditions to the imaging control circuitry 24. Further, the input interface 23 may serve as an interface for manipulating the C-arm 11, and operating the input interface 23 can thus rotate the C-arm 11 about the X axis and set it in a desired position. The imaging direction is determined according to the set position of the C-arm 11.

The imaging control circuitry 24 includes a processor and a memory (not shown in the figures) to control each component of the X-ray imaging stand 3 based on the imaging conditions set via the input interface 23, so that the X-ray imaging stand 3 performs X-ray imaging according to the setting.

The image generation circuitry 25 generates pre-image data and main image data of a breast based on output signals from the X-ray detector 16. In one example, the image generation circuitry 25 applies preprocessing to the output signals from the X-ray detector 16 to generate X-ray images. Such preprocessing for images includes a correction to inter-channel sensitivity unevenness, a correction to a missing part, etc. The image generation circuitry 25 also subjects the generated X-ray images to image processing. For example, the image generation circuitry 25 applies a scatter correction to the generated X-ray images. In tomosynthesis imaging, the image generation circuitry 25 reconstructs volume data based on multiple X-ray images generated for multiple positions of the X-ray tube 18.

The processing circuitry 26 reads the information and the programs from the memory 22 according to an instruction input by the operator via the input interface 23, and controls the computer device 5 based on these. In one example, the processing circuitry 26 is a processor to realize, in addition to existing functions, various functions for acquiring information for the determination of more appropriate conditions after pre-imaging, according to the program or programs read from the memory 22. Here, examples of the functions include an information acquisition function 261, an index calculation function 262, a condition acquisition function 263, and a display control function 264.

The information acquisition function 261 is a function for acquiring information on pre-imaging (a preliminary X-ray imaging) for the breast of a subject. More specifically, the information acquisition function 261 acquires first information including at least one of breast state information indicating the state of a breast at the time of pre-imaging, information on imaging conditions, and/or information on a subject. The information acquisition function 261 also acquires second information which is based on a pre-image acquired by the pre-imaging. The information on pre-imaging here may refer to, for example, breast state information, information on imaging conditions, information on a subject, and a pre-image collected by the mammography apparatus 1 through pre-imaging (a preliminary image). The breast state information contains, for example, at least one of a compressing pressure on the breast, a thickness of the breast, and/or an opposing force (a resistance) of the breast against the compressing pressure. The imaging conditions for pre-imaging are X-ray conditions for the pre-imaging, which include, for example, at least one of a tube voltage kV, a tube current-time product mAs, and/or a radiation quality filter. According to one embodiment, for example, the information on pre-imaging includes, other than the pre-image, at least one of a compressing pressure on the breast, a resistance, a thickness of the breast, a tube voltage kV, a tube current-time product mAs, and/or a radiation quality filter. A thickness of the breast is geometric information determined from the positional relationship between the detection plane 16a and the compression plate 17a. In one example, the information acquisition function 261 acquires the positional relationship between the detection plane 16a and the compression plate 17a based on control signals output from the imaging control circuitry 24 at the time of the pre-imaging, and then acquires the breast thickness based on the acquired positional relationship. Also, the information acquisition function 261 in one example acquires the compressing pressure on the breast based on one or more values from an encoder, a potentiometer, etc., provided at the compression unit 17. The information acquisition function 261 in one example further acquires the opposing force (resistance) received by the compression plate 17a from the breast under compression, based on the correspondence relationship between the compressing pressure on the breast and the breast thickness acquired during the compression. The information acquisition function 261 is an example of an acquirer.

The index calculation function 262 is a function for calculating an index for a breast based on the information on pre-imaging. As the index for a breast, for example, a breast evaluating index including a breast density, a composition of the breast, or the like may be used as appropriate. The breast density here is a ratio of mammary gland tissues to a breast, and it is a quantitatively expressed numerical value. Generally, a breast density can be acquired from the pixel values of a mammogram corresponding to the inside of a breast. More specifically, as a general method, a breast density can be acquired by substituting, into a general formula for calculating a breast density [%], a pixel value of a region in a mammogram that is constituted only by fat tissues, a pixel value of a region in the mammogram that includes mammary gland tissues, and linear attenuation coefficients of fat tissues and mammary gland tissues. The acquired density value may be used as it is as the index for a breast, or it may be classified into one of four types, "extremely dense", "heterogeneous dense", "scattered", and "fatty", using cutoff values and then used. Note that a breast density may be calculated by different methods as appropriate, including, for example, a method of irradiating a breast with X-rays and calculating a content of the mammary glands from the X-ray attenuation coefficient obtained based on the information acquired by the irradiation. A breast composition can be acquired from the ratio of areas in a mammogram corresponding to the inside of the breast. More specifically, in general, a breast composition can be acquired by calculating an index that indicates a content of mammary glands (a breast density [%]) from the ratio [a sum of areas of portions having a density equal to or greater than pectoralis major]/[an area of a region where mammary gland tissues are assumed to have originally existed] in a mammogram, and classifying the index into one of the types "extremely dense", "heterogeneous dense", "scattered", and "fatty". For example, a breast density of 80% or higher is classified as "extremely dense", that of 50% or higher and lower than 80% is classified as "heterogeneous dense", that of 10% or higher and lower than 50% is classified as "scattered", and that of lower than 10% is classified as "fatty". Also for example, a breast density of 50% or higher may be collectively classified as "dense breast", instead of being classified as "extremely dense" or "heterogeneous dense". These methods each represent an example, and different methods may be adopted as appropriate.

In one embodiment, the index calculation function 262 calculates an index including a breast density or a breast composition based on at least one of an imaging condition, breast state information, and/or information on a subject among the information on pre-imaging (that is, information other than a pre-image). The information other than a pre-image is one example of the first information. In one embodiment, for example, the index calculation function 262 calculates an index for a breast by inputting at least one of an imaging condition, breast state information, and/or information on a subject among the information on pre-imaging, into a trained model read from the memory 22. The trained model outputs an index for the breast based on at least one of the imaging condition, the breast state information, and/or the information on the subject among the information on pre-imaging for the breast. Note that, while the data input into the trained model may be any combination of imaging conditions, breast state information, and information on a subject, the embodiment is not limited to this, and the input data may further contain a pre-image, other information acquired from the pre-imaging by the mammography apparatus 1, and so on. In one embodiment, for example, the index calculation function 262 calculates an index for a breast by inputting at least one of an imaging condition, breast state information, and/or information on a subject, and also a pre-image, into a trained model read from the memory 22. The "sum of areas of portions having a density equal to or greater than pectoralis major" may also be called a "mammary gland region". The index calculation function 262 is one example of a calculator.

The condition acquisition function 263 is a function for acquiring imaging conditions for main imaging based on the calculated index. In one example, the memory 22 stores in advance a first table in which indexes for a breast and imaging conditions for main imaging are associated with each another. The condition acquisition function 263 may acquire imaging conditions from the first table in the memory 22 based on the calculated index. The acquired imaging conditions are sent to the imaging control circuitry 24. Also, the condition acquisition function 263 is a function for acquiring, based on the calculated index, image processing conditions for a main image acquired by main imaging. In one example, the memory 22 stores in advance a second table in which indexes for a breast and image processing conditions for a main image are associated with each another. The condition acquisition function 263 may acquire imaging processing conditions from the second table in the memory 22 based on the calculated index. The acquired image processing conditions are sent to the image generation circuitry 25. The condition acquisition function 263 is an example of a condition acquirer.

The display control function 264 is a function for causing the display 27 to display medical images such as pre-images and main images. The display control function 264 is an example of a display controller.

The display 27 includes a display main part for displaying medical images, etc., such as pre-images and main images, internal circuitry for supplying display signals to the display main part, and peripheral circuitry including connectors, cables, or the like for connection between the display main part and the internal circuitry. The display 27 is an example of a display part for displaying medical images, etc., under the control of the processing circuitry 26.

The system control circuitry 28 includes a processor and a memory (not shown in the figures), and serves as a center of the mammography apparatus 1 to control each component.

The network interface 29 is circuitry for connecting the computer device 5 to a network Nw for communication with external devices (not shown in the figures). As the network interface 29, for example, a network interface card (NIC) may be employed.

Note that the computer device 5 and the X-ray imaging stand 3 may be provided as an integral unit.

Next, operations of the mammography apparatus configured as above will be described with reference to the flowcharts in FIG. 3.

The description will assume that the mammography apparatus 1 already stores subject information sent from, for example, the RIS in the memory 22. The subject information contains, for example, a subject ID, an examination part, an examination purpose, an age, a body height, a body weight, a body mass index (BMI), etc. It will also be assumed that a mammography examination is to be conducted on the breast of a subject based on the subject information.

Now, with the mammography apparatus 1, step S10 is performed where the breast of the subject is placed on the detection plane 16*a* and compressed by the compression plate 17*a* according to an operation by an operator, so that the breast is fixed to the detection plane 16*a*. At this time, the mammography apparatus 1 acquires the thickness of the breast, the compressing pressure on the breast, and the resistance, while the breast is in the compressed state.

In step S20 after step S10, the mammography apparatus 1 performs pre-imaging for the fixed breast according to an operation by the operator. More specifically, the mammography apparatus 1 causes the X-ray tube 18 to radiate X-rays in response to the operation by the operator. The X-rays radiated from the X-ray tube 18 transmit through the compression plate 17*a* and the breast and are then detected by the X-ray detector 16. The mammography apparatus 1 here acquires imaging conditions for the pre-imaging and stores them in the memory 22. For example, the mammography apparatus 1 acquires imaging conditions such as a tube voltage kV, a tube current-time product mAs, and a radiation quality filter, and stores them in the memory 22.

In step S30 after step S20, the processing circuitry 26 of the mammography apparatus 1 acquires information on the pre-imaging. In one example, the image generation circuitry 25 of the mammography apparatus 1 receives, from the X-ray detector 16, an output signal corresponding to the X-ray radiation dose detected by the X-ray detector 16, generates a pre-image representing the breast of the subject by applying image processing to this output signal, and stores the pre-image in the memory 22. Accordingly, the processing circuitry 26 acquires the pre-image stored in the memory 22. The processing circuitry 26 also acquires the imaging conditions for the pre-image including, for example, the tube voltage kV, the tube current-time product mAs, and a radiation quality filter, from the memory 22. The processing circuitry 26 also acquires the thickness of the breast under the compression of step S10.

In step S40 after step S30, the processing circuitry 26 calculates an index for the breast based on the information on the pre-imaging. In this example, the processing circuitry 26 with the trained model in the memory 22 calculates an index including a breast composition based on the breast thickness, the tube voltage kV, and the tube current-time product mAs. The calculated index shows an evaluation that the pre-imaged breast is a fatty breast, a breast with scattered mammary glands, a heterogeneous dense breast, or an extremely dense breast.

In step S50 after step S40, the processing circuitry 26 acquires imaging conditions for main imaging based on the calculated index. In one example, the processing circuitry 26 acquires the imaging conditions associated with the index from the first table stored in advance. For example, a tube voltage kV, a tube current-time product mAs, etc. may be acquired as the imaging conditions for the main imaging. The imaging conditions in the case of the index indicating a dense breast may include a slight increase in the compressing pressure prior to the main imaging. For tomosynthesis imaging, imaging conditions such as a sweep angle, a number of images to be acquired, and a compressing pressure are additionally acquired. More specifically, and for example, mammary glands, which make lesions difficult to see, are contained in a fatty breast only in a small amount, and therefore, a fatty breast can be imaged using a lower radiation dose. Accordingly, in the case of the index indicating a fatty breast, imaging conditions that stipulate a smaller X-ray radiation dose are acquired for the main imaging. Also, tomosynthesis imaging for a fatty breast does not require a high resolution in the depth direction since there is little overlap between fat and a lesion. Thus, in the case of the index indicating a fatty breast, imaging conditions that stipulate image acquisition at a sweep angle that gives a small depth are acquired for the main imaging.

In step S60 after step S50, the processing circuitry 26 acquires image processing conditions for a main image based on the calculated index. In one example, the processing circuitry 26 acquires the image processing conditions associated with the index from the second table stored in advance. Examples of the image processing conditions for a main image include a denoising strength, a digital compensation filter (DCF) strength, a frequency enhancement process, a gradation process, a spatial filter, a scatter correction, and so on. For tomosynthesis imaging, image processing conditions including reconstruction parameters such as an iteration number, a slice thickness, and a slice number are additionally acquired. More specifically, and for example, the index indicating a fatty breast can suggest a preference to display a fatty area in a darkened manner, and accordingly, image processing conditions that correspond to a darker window level than before are acquired for the main image.

In step S70 after step S60, the processing circuitry 26 conducts the main imaging for the breast based on the imaging conditions acquired in step S50. Note that the pre-imaging performed in step S20 and this main imaging performed after the pre-imaging are both X-ray imaging targeting the same breast of the subject. The mammography apparatus 1 thus obtains the main image of the breast held still since step S10.

In step S80 after step S70, the processing circuitry 26 processes the main image based on the image processing conditions acquired in step S60.

In step S90 after step S80, the processing circuitry 26 causes the display 27 to display the main image that has undergone the image processing. The main image after the image processing is an outcome of the main imaging and the image processing, which are based on the index calculated upon the pre-imaging, and accordingly, this main imaging allows for easier and better interpretation.

According to an embodiment as described above, the mammography apparatus 1 acquires, as the information on pre-imaging for a breast of a subject, first information including at least one of information on imaging conditions, breast state information indicating the state of the breast, and/or information on the subject, and calculates an index for the breast based on the acquired first information. Note that the index for the breast here is information indirectly obtained from the pre-imaging, and such indirect information can be used as the information for determining more appropriate imaging conditions and image processing conditions. More specifically, based on such an index for a breast, it is possible for the case of, for example, the breast being a fatty breast to determine imaging conditions that stipulate a lower radiation dose and image processing conditions that darken the fatty region. Likewise, based on such an index for a breast, it is possible for the case of, for example, the breast being a dense breast to determine imaging conditions that stipulate a higher radiation dose and image processing conditions that lighten the mammary gland region. As such, according to an embodiment, not only the direct information obtained from the pre-imaging, but also information for determining more appropriate conditions can be acquired. The first information here is information constituted by one or more information sets other than a pre-image acquired by the pre-imaging. Thus, in addition to realizing the advantages discussed above, an embodiment even allows the index for a breast to be obtained without using the pre-image.

Also according to an embodiment, the mammography apparatus 1 calculates the index for a breast by inputting the first information into a trained model adapted to calculate the index for a breast based on the first information. Therefore, according to an embodiment, the index for the breast can be more accurately calculated based on the first information without being bound by the direct information obtained from the pre-imaging. This means that acquisition of the information for determining more appropriate conditions is possible. According to an embodiment, moreover, the mammography apparatus 1 may calculate the index for a breast by inputting the first information and a preliminarily acquired image (preliminary image) into a trained model adapted to calculate the index for a breast based on the first information and the preliminarily acquired image. Thus, according to an embodiment, the index for the breast can be more accurately calculated as compared to the instance of employing a trained model that has been prepared using only the first information as training data.

According to an embodiment, the index for a breast may be a breast evaluating index including a breast density or a composition of the breast. Here, an index for evaluating a breast that includes a breast density or a breast composition is made available before main imaging. Accordingly, in addition to realizing the advantages discussed above, it is possible to determine the conditions for the main imaging by also taking into account at least the breast density or the breast composition. More specifically, the conventional configurations were able to identify a breast composition only after main imaging, and as such, a difficulty in optimizing the imaging conditions for main imaging was involved. Also, the conventional configurations calculated a breast density or a breast composition after main imaging and then utilized the calculated information for subsequent processes. As such, the conventional configurations involved an inconvenience of requiring a time for processing. In contrast, according to an embodiment, a breast density or a breast composition is acquired before main imaging, and therefore, the processing proceeds without such disadvantages. Additionally, according to an embodiment, variations in image quality due to, for example, differences in breast density (a fatty breast, a dense breast, etc.) or breast composition can be suppressed. Further, the index including a breast density covers more detailed values, and therefore, an enhanced accuracy can be expected of the index for a breast, in addition to realizing the advantages discussed above. Also, the index (a breast density) may be used for the calculation of a mean glandular dose (MGD), which is an exposure dose to mammary glands, so that the exposure dose can be more accurately calculated. Note that, conventionally, a result of measuring a breast density was obtained based on a main image and utilized for recommendation of an ultrasound test, notification of a cancer risk, etc., but not for the process for improving conditions for main imaging.

According to an embodiment, determination of the conditions for main imaging may use a breast density or a breast composition included in the index for a breast and a breast thickness included in the first information. In this case, since the conditions for main imaging are determined using a breast density or a breast composition and also a breast thickness, the conditions for main imaging can be determined with more appropriate contents as compared to, for example, a case of determining the conditions using a breast density or a breast composition without a breast thickness. Further, according to an embodiment, image processing conditions are determined before main imaging, and therefore, a mammography test can be conducted in a shorter time as compared to, for example, a case of calculating a breast density or a breast composition from the performed main imaging and then changing or adjusting the image processing conditions.

According to an embodiment, pre-imaging and main imaging performed after the pre-imaging are both X-ray imaging targeting the same breast of a subject. Thus, the pre-imaging and the main imaging are performed on the same compressed state breast, and accordingly, in addition to realizing the advantages discussed above, an index for each of the targeted breasts can be acquired even if the breasts differ from each other.

Modifications

The description of one or more foregoing embodiments has assumed that information acquired as the information on pre-imaging is information other than a pre-image, and it includes imaging conditions, breast state information, and information on a subject. No limitations are intended by this. For example, the information other than a pre-image may be mechanical information and/or geometric information on the pre-imaging for a breast. Such mechanical information contains, for example, at least one of a compressing pressure on the breast, and/or a resistance. The geometric information may be, as a non-limiting example, a breast thickness. Such a modification can also realize the same advantages as those discussed for the one or more embodiments.

The description of one or more foregoing embodiments has assumed that the information on pre-imaging is information other than a pre-image, but this is not a limitation. For example, the information on pre-imaging may be information based on a pre-image acquired by this pre-imaging. As the information based on a pre-image, for example, the pre-image itself, a statistical value (e.g., a mean value, a median value, etc.) from the pixel values of the breast region in the pre-image, and so on may be used as appropriate. In this case, it can be expected that the obtained index for a breast has more appropriate contents, in addition to realizing the advantages discussed above. Note that such a statistical value of the pixel values is not limited to a mean value, a median value, or the like, and a range of the pixel values (e.g., an upper limit value and a lower limit value) may also be used.

Furthermore, for example, the information on pre-imaging may contain both the information other than a pre-image acquired by the pre-imaging and the information based on the pre-image. In this case, the index for a breast is calculated using the information other than the pre-image and the information based on the pre-image, and therefore, it can be expected that the obtained index for the breast has even more appropriate contents, in addition to realizing the advantages discussed above.

The description of one or more foregoing embodiments has assumed that the information other than a pre-image is information for X-ray imaging which includes, for example, a breast thickness, a tube voltage kV, a tube current-time product mAs, and so on, but no limitations are intended by this. For example, the information other than a pre-image may further include information on a subject acquired by the mammography apparatus 1 before the main imaging to be performed after the pre-imaging. As the information on a subject, for example, information on the body of the subject may be used as appropriate, and such information may be one or more items of the subject information acquired from the RIS by the processing circuitry 26 (e.g., an age, a body height, a body weight, a BMI, etc.), a breast thickness and a compressing pressure on the breast which are acquired from the pre-imaging, and so on. In this case, the index for a breast is calculated by further taking into account the information on the subject, and therefore, it can be expected that the obtained index for the breast has even more appropriate contents, in addition to realizing the advantages discussed above.

The description of one or more foregoing embodiments has also assumed that imaging conditions for main imaging and image processing conditions are both acquired based on the index for a breast, but the configuration is not limited to this. For example, the operation may be conducted in such a manner that, among the imaging conditions for main imaging and the image processing conditions, at least the former or at least the latter is acquired. Nevertheless, for the sake of determining optimum conditions, it is preferred that the imaging conditions for main imaging and the image processing conditions be both acquired.

The description of one or more foregoing embodiments has assumed applications to general mammography imaging and tomosynthesis imaging, but no limitations are intended by this. For example, the embodiments are suitably applicable to any of biopsy imaging, zoom imaging, spot imaging, etc.

In the case of biopsy imaging, for example, since an index such as a breast density can be obtained from the result of pre-imaging even if the whole breast is not imaged, the embodiments are very advantageous over the conventional biopsy imaging which required an image of the whole breast. A particularly effective processing for biopsy imaging would be, as one example of determining imaging conditions for main imaging based on the index, increasing of the X-ray radiation dose according to the breast density. With this processing, the biopsy imaging is given an enhanced capability of visibly showing calcification, so that a puncture can be securely guided to a living tissue desired to be extracted.

Further, for example, in the case of zoom imaging or spot imaging (imaging with a limited irradiation range), the embodiments likewise enable an index such as a breast density to be obtained from the result of pre-imaging even if the whole breast is not imaged, and therefore, the embodiments provide a large advantage wherein the necessity of performing main imaging for the purpose of acquiring an image of the whole breast is eliminated. More specifically, zoom imaging and spot imaging are basically taken from 2D imaging corresponding to the pre-imaging, and therefore, a breast composition can be identified beforehand by the 2D imaging. Note that it is not normally the case that only zoom imaging is performed, but there may be an instance where zoom imaging is performed at a later date from the completion of 2D imaging. In such an instance, the embodiments do not necessitate the retrieval of the past 2D image or similar work at the timing right before the later zoom imaging, and thus, the embodiments are very advantageous.

While the description of the foregoing embodiments has not explicitly discussed change of a workflow based on the index for a breast, the embodiments do not limit such workflow changes. For example, the processing circuitry 26 may change the workflow after pre-imaging based on the index for a breast. More specifically, the processing circuitry 26 in one example realizes, as shown in FIG. 4, a determination function 265 according to one or more programs stored in the memory 22 in a similar manner to each of the functions described above.

The determination function 265 is a function for determining, based on the index calculated by the index calculation function 262, a process to be performed after pre-imaging. For example, the determination function 265 may determine the process based on the index for a breast and the breast thickness contained in the information on the pre-imaging. The index for a breast here may include a breast density, a breast composition, or the like. The determined process here includes at least one of a first process, a second process, and/or a third process. The first process relates to at least one of the imaging conditions for main imaging performed after preliminary X-ray imaging, and/or the image processing conditions. The second process relates to a cancellation of the main imaging. The third process relates to additional imaging. Examples will be given in more concrete terms. As one example, a process for canceling tomosynthesis imaging may be determined for a thin breast or a fatty breast, or instead of canceling the tomosynthesis imaging, a process for adjusting the imaging conditions or the image processing conditions may be determined for such breasts. On the other hand, for a thick breast, a process for canceling the whole main imaging and also reserving an ultrasound diagnosis may be determined, or instead of canceling the main imaging, a process for adjusting the imaging conditions or the image processing conditions may be determined. Also, for a breast having a high absorber internal portion, such as a breast including an implant or a breast feeding an infant, a process for canceling the main imaging or a process for adjusting the conditions may be determined as in the case of a thick breast, since such breasts tend to show a high tube current-time product mAs and they are measured to have a high breast density. In one example, the determination function 265 is able to make such determinations based on imaging conditions for the main imaging that have been acquired by the condition acquisition function 263 referring to a table in which indexes for a breast and processes to be determined are associated with each other. Note that this table may further include identification information of doctors additionally associated with the indexes for a breast and the processes to be determined. That is, as mentioned earlier, it is often the case that the relationship between the index for a breast and a determined process could vary greatly depending on developments in mammography technologies, policies of doctors, etc. The determination function 265 can also cope with such situations by, for example, referring to the table and determining a process based on the index for a breast. Note that the determined process may be one of the first process, the second process, and the third process. The determined process may instead be a combination of two non-contradictory processes, e.g., a combination of the first process for main imaging and the third process for additional imaging. The determination function 265 is an example of a determiner.

Here, the first process is a process related to main imaging and includes at least one of imaging conditions for the main imaging and/or the image processing conditions. The first process may additionally include a process for canceling tomosynthesis imaging among a normal imaging set constituted by mammography imaging (2D imaging) and tomosynthesis imaging. For example, in the case of conducting X-ray imaging in the order of tomosynthesis imaging and then 2D imaging, the determined first process may include canceling the tomosynthesis imaging and performing only the 2D imaging. Also for example, in the case of conducting X-ray imaging in the order of 2D imaging and then tomosynthesis imaging, the determined first process may include terminating the X-ray imaging upon finishing the 2D imaging.

The second process is a process for canceling X-ray imaging (main imaging) for a breast such as mammography imaging (2D imaging) and tomosynthesis imaging. The second process may include a process for encouraging the use of a medical image diagnostic apparatus such as an ultrasound diagnostic apparatus, different from the mammography apparatus.

As the third process, a process for registering (or tentatively registering) an order for additional imaging, a process for recommending additional imaging, etc. may be adopted as appropriate.

The remaining aspects are the same as those described for the foregoing one or more embodiments.

According to the configuration of the modification as described above, after the index is calculated by steps S10 to S40 in a manner similar to the above, step S41 is performed as shown in FIG. 5.

In step S41, the processing circuitry 26 determines, based on the calculated index, a process to be performed after the pre-imaging. More specifically, the processing circuitry 26 determines the process based on, for example, the breast composition included in the index and the breast thickness included in the information on the pre-imaging. The processing circuitry 26 here may use the breast density instead of the breast composition.

In step S42 after step S41, the processing circuitry 26 determines whether or not the determined process is the second process for canceling the main imaging. If the determination result shows that the process is the second process (step S42: Yes), the operation transitions to step S43, and otherwise (step S42: No) the operation transitions to step S44.

In step S43, the processing circuitry 26 conducts the second process for canceling the main imaging and terminates the operation.

In step S44, the processing circuitry 26 determines whether or not the process determined in step S41 is the third process for additional imaging. If the determination result shows that the process is the third process (step S44: Yes), the operation transitions to step S45, and if the determination result is contrary (step S44: No), the operation transitions to step S50.

In step S45, the processing circuitry 26 conducts the third process for additional imaging. For example, the processing circuitry 26 conducts a process for registering (or tentatively registering) an order for additional imaging, a process for recommending additional imaging, or the like. It should be noted that, for a dense breast in a diagnosis phase (not an examination phase), a safer outcome would be attained if additional imaging is conducted. Thus, for example, in the case of secondary examination which includes a diagnosis phase, the processing circuitry 26 may register an order for the additional imaging. In other instances, if a lesion is suspected in the primary examination, an additional imaging may be conducted. In any case, an order for the additional imaging may be automatically registered (tentatively registered) or recommended, and such a message may be presented on the display 27 through a pop-up window, etc., so that inadvertent omission of the imaging can be prevented. If no additional imaging is conducted, the order may be deleted upon, for example, completion of the examination. After step S45, the operation transitions to step S50.

Subsequently, step S50 and onward are performed in the manner as described above.

According to the modification as shown in FIGS. 4 and 5, the processing circuitry 26 determines, based on the calculated index, a process to be performed after the pre-imaging. This allows for a change of the workflow based on the index, and therefore, in addition to realizing the advantages discussed above for one or more embodiments, the processing after the pre-imaging can be adjusted toward a better outcome while improving the conditions for the main imaging. According to the modification, further, the processing circuitry 26 determines the process based on the breast density or the breast composition included in the index for a breast and the breast thickness included in the information on the pre-imaging (i.e., the first information). As such, the process to be performed after the pre-imaging can be appropriately determined according to the breast thickness, the breast density, etc.

Also according to the modification, the determined process includes at least one of the first process, the second process, and/or the third process, wherein the first process relates to at least one of the imaging conditions for main imaging performed after preliminary X-ray imaging and/or the image processing conditions, the second process relates to a cancellation of the main imaging, and the third process relates to additional imaging. Thus, which of the process for the imaging conditions for the main imaging or the image processing conditions, the process for canceling the main imaging, and/or the process for additional imaging should be performed can be determined based on the index after the pre-imaging.

While the description of the modification has mentioned that the third process for additional imaging is performed in the case of the index for a breast indicating a dense breast, the modification is not limited to this. The processing circuitry 26 may perform the third process for additional imaging based on, for example, the index for a breast and also a result of CAD on the breast. For example, the third process for additional imaging may be performed in response to the index for a breast indicating a dense breast and also the result of CAD indicating a positive. Such a form of the modification allows the third process to be performed even more appropriately, while realizing the advantages of the modification discussed above.

According to at least one embodiment described above, it is possible to acquire not only the direct information obtained from the pre-imaging, but also information for determining more appropriate conditions.

The term "processor" or the like used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (FPGA)), and so on. The processor reads and executes a program or programs stored in the memory to realize intended functions. If, for example, the processor is a CPU, the processor reads and executes the program or programs stored in storage circuitry to realize the functions. If, for example, the processor is an ASIC, the functions are directly incorporated into circuitry of the processor in the form of a logic circuit, instead of corresponding programs being stored in storage circuitry. Each processor in the embodiments, etc., is not limited to a single circuit-type processor, and multiple independent circuits may be combined as one processor to realize the intended functions. Furthermore, multiple components or features as given in FIGS. 1 and 4 may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments may be made without departing from the spirit of the inventions. The accompanying claims and their equivalents are intended to cover such forms or modifications as would fall within the scope and spirit of the inventions.

The invention claimed is:

1. A mammography apparatus, comprising:
processing circuitry configured to:
acquire, as information on preliminary X-ray imaging for a breast of a subject, first information including at least one of an imaging condition, breast state information indicating a state of the breast, and/or information on the subject; and
calculate an index for the breast based on the first information,
wherein the processing circuitry is further configured to acquire a preliminary image collected by the preliminary X-ray imaging and calculate the index for the breast based on the first information and the preliminary image; and
wherein the processing circuitry is further configured to calculate the index for the breast by inputting the first information and the preliminary image into a trained model configured to calculate the index for the breast based on the first information and the preliminary image.

2. The mammography apparatus according to claim 1, wherein the breast state information includes at least one of a compressing pressure on the breast and/or a thickness of the breast.

3. The mammography apparatus according to claim 1, wherein the index for the breast is a breast evaluating index including a breast density or a breast composition.

4. The mammography apparatus according to claim 1, wherein the processing circuitry is further configured to determine a process to be performed after the preliminary X-ray imaging based on the calculated index for the breast.

5. The mammography apparatus according to claim 4, wherein the processing circuitry is further configured to determine the process based on the index for the breast and a thickness of the breast, the thickness of the breast being included in the first information.

6. The mammography apparatus according to claim 4, wherein the process includes at least one of a first process, a second process, and/or a third process, wherein the first process relates to at least one of imaging conditions for main imaging after the preliminary X-ray imaging and/or image processing conditions, the second process relates to a cancellation of the main imaging, and the third process relates to additional imaging.

7. The mammography apparatus according to claim 1, wherein the processing circuitry is further configured to acquire the information on the subject before main imaging to be performed after the preliminary X-ray imaging.

8. A mammography apparatus, comprising:
processing circuitry configured to
  acquire, as information on preliminary X-ray imaging for a breast of a subject, first information including at least one of an imaging condition, breast state information indicating a state of the breast, and/or information on the subject; and
  calculate an index for the breast based on the first information,
  wherein the processing circuitry is further configured to calculate the index for the breast by inputting the first information into a trained model configured to calculate the index for the breast based on the first information.

9. The mammography apparatus according to claim 8, wherein the index for the breast is a breast evaluating index including a breast density or a breast composition.

10. The mammography apparatus according to claim 8, wherein the processing circuitry is further configured to determine a process to be performed after the preliminary X-ray imaging based on the calculated index for the breast.

11. The mammography apparatus according to claim 10, wherein the processing circuitry is further configured to determine the process based on the index for the breast and a thickness of the breast, the thickness of the breast being included in the first information.

12. The mammography apparatus according to claim 10, wherein the process includes at least one of a first process, a second process, and/or a third process, wherein the first process relates to at least one of imaging conditions for main imaging after the preliminary X-ray imaging and/or image processing conditions, the second process relates to a cancellation of the main imaging, and the third process relates to additional imaging.

13. The mammography apparatus according to claim 8, wherein the preliminary X-ray imaging and main imaging after the preliminary X-ray imaging are both X-ray imaging targeting the breast of the subject.

14. A mammography apparatus, comprising:
processing circuitry configured to
  acquire, as information on preliminary X-ray imaging for a breast of a subject, first information including at least one of an imaging condition, breast state information indicating a state of the breast, and/or information on the subject; and
  calculate an index for the breast based on the first information;
  wherein the processing circuitry is further configured to determine a process to be performed after the preliminary X-ray imaging based on the calculated index for the breast; and
  wherein the determined process includes at least one of a first process, a second process, and/or a third process, wherein the first process relates to at least one of imaging conditions for main imaging after the preliminary X-ray imaging and/or image processing conditions, the second process relates to a cancellation of the main imaging, and the third process relates to additional imaging.

15. The mammography apparatus according to claim 14, wherein the processing circuitry is further configured to determine the process based on the index for the breast and a thickness of the breast, the thickness of the breast being included in the first information.

16. A mammography apparatus, comprising:
processing circuitry configured to
  acquire, as information on preliminary X-ray imaging for a breast of a subject first information including at least one of an imaging condition, breast state information indicating a state of the breast, and/or information on the subject; and
  calculate an index for the breast based on the first information,
  wherein the preliminary X-ray imaging and main imaging after the preliminary X-ray imaging are both X-ray imaging targeting the breast of the subject.

* * * * *